(12) United States Patent
Xu et al.

(10) Patent No.: US 6,172,376 B1
(45) Date of Patent: Jan. 9, 2001

(54) METHOD AND SYSTEM FOR MEASURING PARTICLES IN A LIQUID SAMPLE

(75) Inventors: Mindi Xu, Naperville; Weiching Li, Chicago, both of IL (US)

(73) Assignee: American Air Liquide Inc., Walnut Creek, CA (US)

( * ) Notice: Under 35 U.S.C. 154(b), the term of this patent shall be extended for 0 days.

(21) Appl. No.: 09/152,520

(22) Filed: Sep. 14, 1998

Related U.S. Application Data

(60) Provisional application No. 60/069,960, filed on Dec. 17, 1997.

(51) Int. Cl.[7] .................................................... B08B 13/00
(52) U.S. Cl. ...................... 250/574; 210/745; 134/103.1
(58) Field of Search .................................. 250/574–577, 250/222.1; 68/12.02; 134/95.3, 99.1, 111, 113, 103.1; 210/745; 95/6, 46

(56) References Cited

U.S. PATENT DOCUMENTS

| | | |
|---|---|---|
| 3,200,700 | 8/1965 | Topol . |
| 3,236,602 | 2/1966 | Isreeli . |
| 3,345,910 | 10/1967 | Rosin et al. . |
| 3,480,784 | 11/1969 | Pierce . |
| 3,560,099 | 2/1971 | Boe et al. . |
| 3,915,570 | 10/1975 | Skala . |
| 4,181,009 | 1/1980 | Williamson . |
| 4,466,257 | 8/1984 | Pefley et al. . |
| 4,783,599 | 11/1988 | Borden . |
| 4,986,659 | 1/1991 | Bachalo . |
| 4,989,978 | 2/1991 | Groner . |
| 5,012,119 | 4/1991 | Rhiner . |
| 5,017,775 | 5/1991 | Granz et al. . |
| 5,033,858 | 7/1991 | Twerdochlib et al. . |
| 5,061,070 | 10/1991 | Batchelder et al. . |
| 5,425,803 | 6/1995 | van Schravendijk et al. . |
| 5,490,187 | 2/1996 | VanSiclen et al. . |
| 5,490,392 | 2/1996 | Williams et al. . |
| 5,498,377 | 3/1996 | Ozaki et al. . |
| 5,517,870 | 5/1996 | Kurimura et al. . |
| 5,583,625 | 12/1996 | Miura et al. . |
| 5,628,362 | 5/1997 | Rew et al. . |
| 5,645,625 | 7/1997 | van Schravendijk et al. . |
| 5,647,386 | 7/1997 | Kaiser . |
| 5,702,358 | 12/1997 | Witherspoon et al. . |
| 5,772,736 | 6/1998 | van Schravendijk et al. . |

FOREIGN PATENT DOCUMENTS

| | | |
|---|---|---|
| 0434966 | 7/1991 | (EP) . |
| 0598424 | 5/1994 | (EP) . |
| 0 908 664 | 4/1999 | (EP) . |
| 61-176858 | 8/1986 | (JP) . |
| 61-181939 | 8/1986 | (JP) . |
| 63-158106 | 7/1988 | (JP) . |

OTHER PUBLICATIONS

European Search Report issued in European Application No. EP 98 40 3174.

Primary Examiner—Stephone B. Allen
(74) Attorney, Agent, or Firm—Burns, Doane, Swecker & Mathis, L.L.P.

(57) ABSTRACT

Provided are a method and apparatus for measuring particles in a liquid sample. The method involves introducing a liquid sample into a heat exchanger, thereby cooling the sample to a predetermined temperature. A particle measurement is performed on the cooled sample by introducing the cooled sample into a particle detector. The method and apparatus in accordance with the invention effectively suppress bubbles present in a liquid chemical sample being measured, thereby allowing for accurate particle measurements. The invention has particular applicability in the semiconductor and pharmaceutical manufacturing industries.

20 Claims, 5 Drawing Sheets

METHOD AND SYSTEM FOR MEASURING PARTICLES IN A LIQUID SAMPLE

CROSS-REFERENCE TO RELATED APPLICATIONS

This application claims the benefit of priority under 35 U.S.C. §119(e) of U.S. provisional application Ser. No. 60/069,960, filed Dec. 17, 1997, the contents of which are herein incorporated by reference.

BACKGROUND OF THE INVENTION

1. Field of the Invention

The present invention relates to a novel method of measuring particles in a liquid sample. The invention also relates to a system for measuring particles in a liquid sample. The invention allows for effective suppression of bubbles in liquid samples, and has particular applicability in the semiconductor and pharmaceutical manufacturing industries.

2. Description of the Related Art

In many industries, such as the semiconductor and pharmaceutical manufacturing industries, it is important that the process chemicals employed have very low particle concentrations. Typical chemicals employed in the semiconductor and pharmaceutical manufacturing industries include, for example, ammonium hydroxide, hydrogen peroxide, sodium hydroxide, hydrofluoric acid, nitric acid, sulfuric acid, phosphoric acid, acetic acid, isopropyl alcohol, tetramethylammonium hydroxide, de-ionized water and mixtures thereof. It is desirable that concentrations of less than 10 particles (>0.2 $\mu$m) per milliliter be maintained in such chemicals.

The particles present in the chemicals may be present in solid form, in colloid form or in a combination of those two forms. In any case, such particles are harmful to the manufacturing processes and the product formed, and bring about a reduction in the product yield.

Particles in liquids, or liquid-born particles, are conventionally monitored for quality control and production assurance with an optical-type particle counter or monitor. In such instruments, a sample of the liquid laden with particles is illuminated by a laser beam and light is scattered by the particles. The scattered light is collected by the instrument, and particle counts and size information is generated based on the scattered light measurements.

In addition to the particles in the liquid chemicals, micro-bubbles are also present. The micro-bubbles can be attached to the particles or can be freely dispersed in the liquid. In contrast to the particles in solution, micro-bubbles are not always detrimental to the products being formed.

It has been found that during particle measurement with optical-type particle instruments, micro-bubbles exhibit similar light scattering characteristic to particles. As a result, optical-type particle instruments cannot distinguish between the bubbles and the particles, and bubbles will be counted as particles. Chemicals which are actually within process specifications may, therefore, be wasted due to the artificially high particle counts resulting from the mischaracterization of micro-bubbles as particles.

A countermeasure which has been proposed for eliminating the effects of micro-bubbles on liquid-born particle measurements is suppression of the micro-bubbles by pressure. Optical-type particle counters having a compression chamber are commercially available, for example, the Particle Measuring Systems Inc. CLS-700 and the HIAC/ROYCO 8000A systems. In such systems, compressed air or nitrogen is applied directly to the liquid surface. This is intended to compress the gas in the bubbles back into the liquid.

It has, however, been found that while relatively large bubbles can be suppressed in this manner, a multitude of smaller bubbles are formed by the break-up of the larger bubbles and/or by a mere reduction in size of the larger bubbles. In addition, bubbles formed by the chemical's decomposition gases, regardless of size, cannot effectively be compressed back into the liquid.

Another method for dealing with the presence of micro-bubbles is disclosed in U.S. Pat. No. 4,783,599, to Borden. In that patent a system is described which distinguishes non-contaminant bubbles from contaminant particles. The substantially spherical bubbles are detected by symmetrically spaced photodiodes. The irregularly shaped contaminant particles are detected and the presence of the bubbles are negated by the detection system. This method, however, may be limited to large bubbles and irregularly shaped particles. Spherical particles would necessarily be mischaracterized as bubbles.

To meet the requirements of the semiconductor and pharmaceutical manufacturing industries and to overcome the disadvantages of the related art, it is an object of the present invention to provide a novel method of measuring particles in a liquid sample.

It is also an object of the present invention to provide a system for measuring particles in a liquid sample, with which the inventive method can be practiced.

The method and apparatus in accordance with the invention allow for the effective suppression of bubbles present in a liquid chemical sample, thereby allowing for accurate particle measurements.

Other objects and advantages of the present invention will become apparent to one of ordinary skill in the art upon review of the specification, drawings and claims appended hereto.

SUMMARY OF THE INVENTION

The foregoing objectives are met by the methods of the present invention. According to a first aspect of the present invention, a novel method of measuring particles in a liquid sample is provided. In the method, a liquid sample is introduced into a heat exchanger, thereby cooling the sample to a predetermined temperature. A particle measurement is performed on the cooled sample by introducing the cooled sample into a particle detector. The method provides an effective solution to the problems associated with liquid-borne particle measurements by suppressing, via temperature control, micro-bubbles in the sample.

According to a second aspect of the invention, a system for measuring particles in a liquid sample is provided. The system includes a heat exchanger connected to receive a liquid sample from a liquid source. Also included are an inlet conduit through which the liquid sample is introduced to the heat exchanger, an outlet conduit through which the liquid sample exits the heat exchanger and means for controlling the temperature of the liquid sample exiting the heat exchanger to a predetermined temperature. That temperature is less than the temperature of the liquid sample entering the heat exchanger. A particle detector is connected to receive the cooled liquid sample from the heat exchanger.

BRIEF DESCRIPTION OF THE DRAWINGS

The objects and advantages of the invention will become apparent from the following detailed description of the preferred embodiments thereof in connection with the accompanying drawings, in which like reference numerals denote like reference numerals, and in which.

DETAILED DESCRIPTION OF THE PREFERRED EMBODIMENTS OF THE INVENTION

Through the invention, it has been found that micro-bubbles in liquid chemicals are particularly sensitive to the liquid temperature. The gases making up the micro-bubbles dissolve in the liquid at low temperatures, thereby eliminating the bubbles from the solution. Thus, the presence of bubbles in a liquid chemical can be effectively suppressed by cooling the chemical prior to its introduction into a particle measurement system. The cooling temperature is generally chemical specific, and is preferably a predetermined temperature at which the bubbles are at a minimum. This allows for accurate particle measurements of liquid chemicals.

Figure 1:
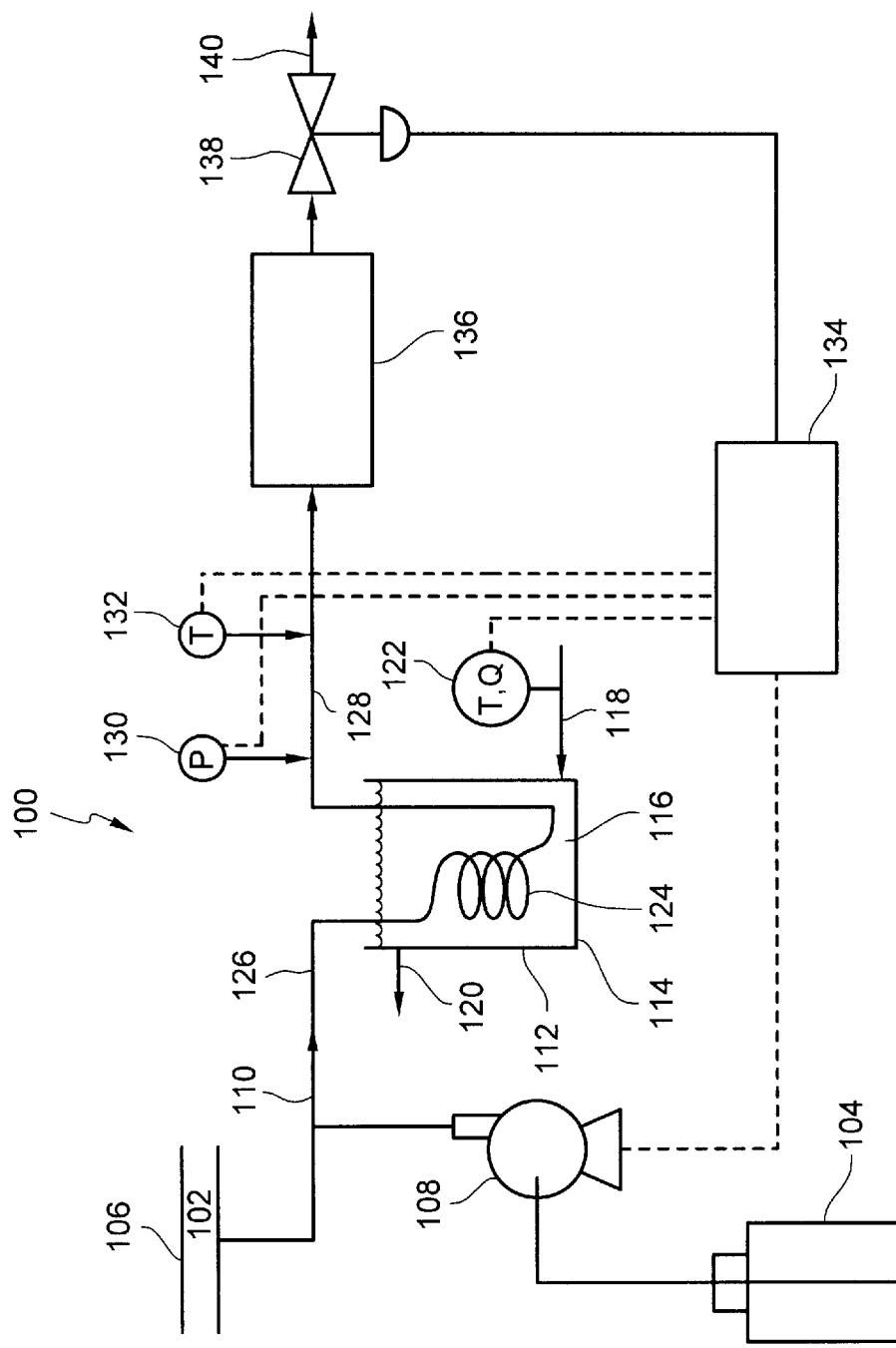
FIG. 1 illustrates a system for measuring particles in a liquid chemical in accordance with the invention.

The method and system of the present invention will be described with reference to FIG. 1, which illustrates an exemplary system 100 for measuring particles in a liquid chemical in accordance with an exemplary aspect of the invention. A continuous sample of the liquid chemical 102 to be measured is removed from, for example, a holding vessel 104 or from a chemical distribution conduit 106.

The sample can be transported by a pump 108 or, alternatively, can be introduced by the system static pressure via conduit 110 into a heat exchanger 112. The chemical sample can thereby be pumped or pushed via the system pressure through the whole system in a continuous manner.

The heat exchanger 112 cools the sample passing therethrough to a predetermined temperature at which micro-bubbles existing in the liquid are effectively suppressed. In accordance with this exemplary embodiment, the heat exchanger 112 includes a container 114 which holds a coolant 116. The coolant can be water or any commercially available liquid or gas coolant which can maintain the temperature of the sample to the desired temperature, and which is compatible with the materials of the system.

Coolant 116 is introduced into container 114 through coolant inlet conduit 118 and is removed therefrom through coolant outlet conduit 120. A temperature and flow controller 122 on coolant inlet conduit 118 controls the flow rate of the coolant introduced into container.

A coil 124 is immersed in the coolant in container 114. The sample passes from sample inlet conduit 126 through coil 124 and out of the heat exchanger through sample outlet conduit 128. The coil is constructed of a material which is compatible with both the sample and the heat exchange fluid. Preferably, the coil is constructed of a corrosion resistant material, such as TEFLON. Since the sample flows inside a clean tube, the sample will not be contaminated by the coolant or heat exchange surface.

A pressure sensor 130 or a flow meter, such as an ultrasonic flow meter commercially available from Honda Electronics, through Nano-Master U.S.A., Inc., Austin, Tex., is provided in sample outlet conduit 128 for monitoring the sample pressure or flow rate, respectively. These instruments are useful for monitoring flow of the sample through the system, and can be connected to a main controller 134. To automatically control flow of the sample through the system, the main controller can be, in turn, connected to pump 108 or valve 138. Suitable control means usable for controller 134 are known in the art and include, for example, one or more programmable logic controllers (PLCs) or microprocessors.

A temperature sensor 132 is also provided in sample outlet conduit 128 or inside the heat exchanger towards the outlet thereof for monitoring the temperature of the sample exiting the heat exchanger. The temperature sensor can be disposed outside of and in contact with, within, or embedded in the wall of the sample conduit. Temperature sensor 132 is preferably a thermocouple or other temperature probe encapsulated in a chemical corrosion material such as TEFLON. Suitable thermocouples are commercially available, for example, from C-temp of Anaheim, Calif.

Connected to temperature sensor 132 as well as temperature and flow controller 122 is main controller 134, which together can control and operate the heat exchanger. The controller for operation of the heat exchanger can be the same or different as that described above with reference to the flow controller.

Control of the liquid chemical sample temperature in accordance with one aspect of the invention can be accomplished as follows. The temperature of the sample as it exits the heat exchanger through sample outlet conduit 128 is monitored with temperature sensor 132. The measurement signal from temperature sensor 132 is sent to main controller 134, in which the temperature set point was previously programmed. Based on the measurement signal, main controller 134 adjusts, via temperature and flow rate controller 122, the flow rate of the coolant 116 introduced into the heat exchanger through coolant inlet conduit 118. In this way, the temperature of the sample can be maintained at a predetermined temperature such that the bubbles in solution are effectively suppressed.

The liquid chemical sample exiting the heat exchanger, which is essentially free of bubbles, passes through sample outlet conduit 128 into a particle sensor 136 for particle measurement. The sample flow rate into the particle sensor is adjusted to the flow rate specified by the particle sensor with a valve 138 at the outlet of the particle sensor.

Following particle measurement, the sample is discharged from the particle sensor via conduit 140. The sample exiting the particle sensor is directed to a drain or, alternatively, back to the chemical supply from which the liquid chemical was originally taken.

Figure 2:
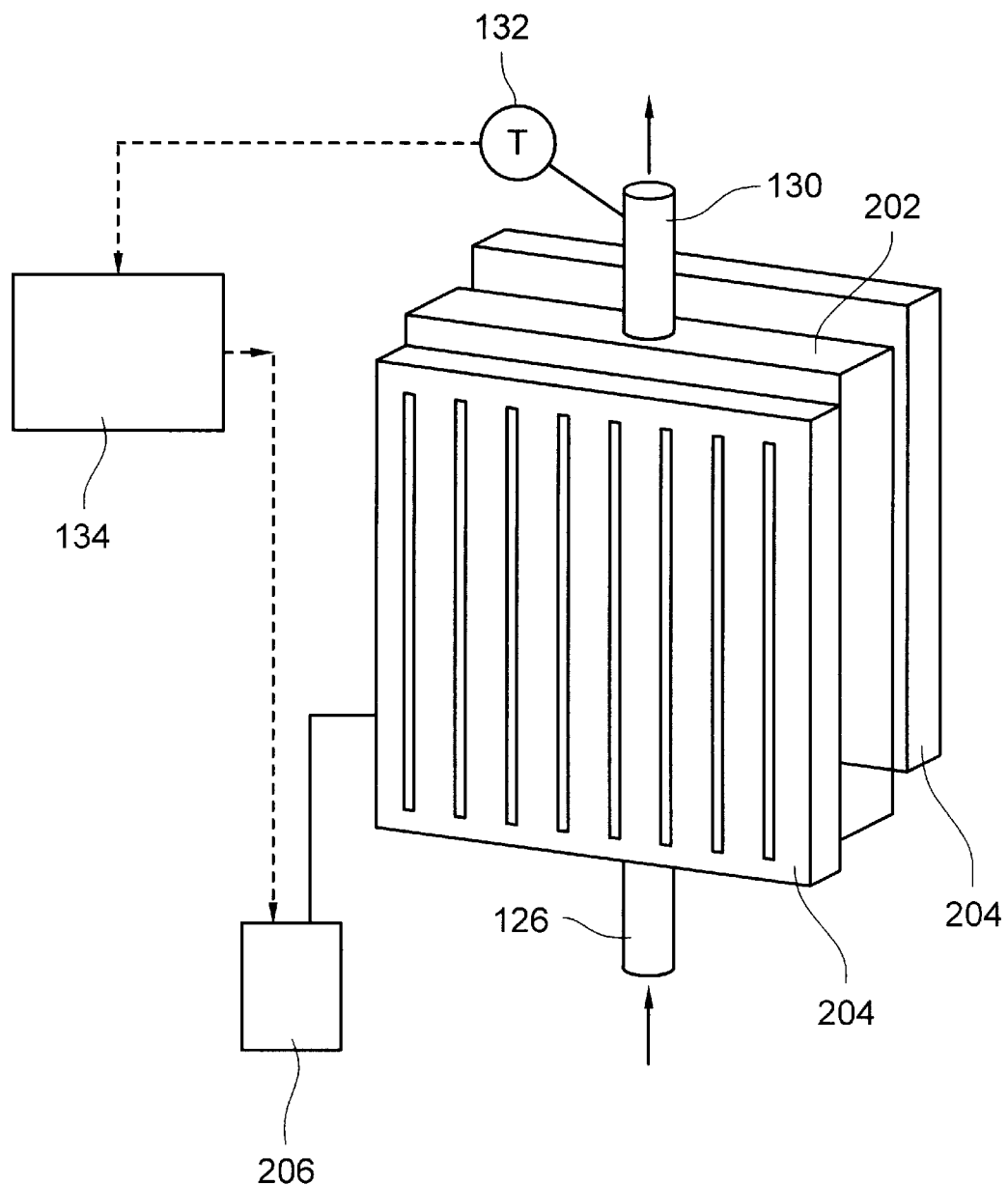
FIG. 2 illustrates an exemplary heat exchanger for suppressing bubbles in a liquid chemical which can be used with the system shown in FIG. 1.

According to another embodiment of the invention, the heat exchanger 112 can be configured as shown in FIG. 2, in which a rectangularly-shaped container 202 made of a corrosion resistant material, such as TEFLON, receives the liquid chemical sample via sample inlet line 126. While the illustrated container is rectangular in shape, containers of other shapes are also envisioned. For example, a container which is cylindrical or annular in shape can be employed.

Attached to the container 202 is one or more thermoelectric cooler 204 for removing heat from the sample. The surface(s) of the container 202 provides the heat exchange surface between the liquid sample and the cooler. Suitable thermoelectric coolers are commercially available, for example, from Mellor.

Preferably, two thermoelectric coolers 204 are disposed on opposite sides of the rectangular container to provide even and efficient cooling of the sample. In the case of this preferred two cooler system, the surface area can be maximized by making the other four surfaces of the rectangular container as small as possible. This has the effect of increasing heat exchange capacity.

The means to control the sample temperature for this embodiment are identical to those described above with reference to FIG. 1, except that an electric current controller 206 is employed to control the thermoelectric coolers in place of the temperature and flow controller.

Because the liquid chemicals which may be analyzed may have different heat capacities and may require control to different temperatures for optimally suppressing the micro-bubbles, the thermoelectric coolers preferably have an adjustable temperature range for convenient control of the liquid sample temperature inside the container. Typically, D.C. power is required by the thermoelectric coolers in a specific power range, depending on the amount of heat to be removed from the sample.

From the above, it should be clear to those skilled in the art that various heat exchanger configurations can be employed without departing from the scope of the invention. For example, the sample can be made to flow through one or more tube surrounded by the coolant, such as in a coaxial tube, or using other known types of heat exchangers.

The effectiveness of temperature control is a function of the heat exchange area, for example, based on the dimensions of the cooling coil or the heat exchange area in the case of a thermoelectric cooler. The heat exchange area can be determined based on following equations:

$$A = Q/U\Delta t$$

where A is the heat exchange area, Q is the total heat load, U is the mean overall heat transfer coefficient, and $\Delta t$ is the logarithmic-mean temperature difference, which can be calculated according to the following equation:

$$\Delta t = \frac{(t_{s1} - t_{c2}) - (t_{s2} - t_{c1})}{\ln\left(\frac{t_{s1} - t_{c2}}{t_{s2} - t_{c1}}\right)}$$

where $t_{s1}$ is the temperature of the liquid sample introduced into the heat exchanger, $t_{s2}$ is the temperature of the liquid sample leaving the heat exchanger, $t_{c1}$ is the temperature of the coolant introduced into the heat exchanger, and $t_{c2}$ is the temperature of the coolant leaving the heat exchanger. The temperature $t_{s1}$ is typically room temperature, and the temperature $t_{s2}$ is typically below 18° C. and above the liquid freezing point, preferred in the range of 10 to 15° C.

Of course, as discussed above, the optimal temperature and workable temperature range is dependent on the specific chemical being measured. Such workable temperature ranges and optimal temperatures at which bubbles are minimized can be determined experimentally.

The following examples illustrate that the systems and methods of the invention are particularly effective in the suppression and elimination of micro-bubbles during particle measurement of liquid chemicals. In each of the examples, the apparatus illustrated in FIG. 1 was employed for the particle measurement.

EXAMPLE 1

Three TEFLON bottles were each filled with 500 ml of electronic grade 30% hydrogen peroxide ($H_2O_2$) solution, and caps were secured to the bottles. One of the bottles was held as a control sample. The other two bottles were each shaken with an electric shaker at 150 rpm for 1 hour to artificially create micro-bubbles in the liquid samples. Each of the shaker bottles was removed from the shaker and a particle measurement was performed using a PMS HSLIS M-65 particle monitor at different liquid sample temperatures.

A ¼ inch PFA TEFLON tube coil in a refrigerated circulating bath was used as a heat exchanger to control the sample temperature. The sample from one of the shaker bottles was controlled to a temperature of 12° C. and the sample from the other shaker bottle was controlled at 25° C. The sample was pumped with a TEFLON diaphragm pump through the heat exchanger coil immersed in the refrigerated coolant bath to the particle monitor for particle measurement. Particle measurement of the hydrogen peroxide control sample which was not shaken was likewise made.

Figure 3:
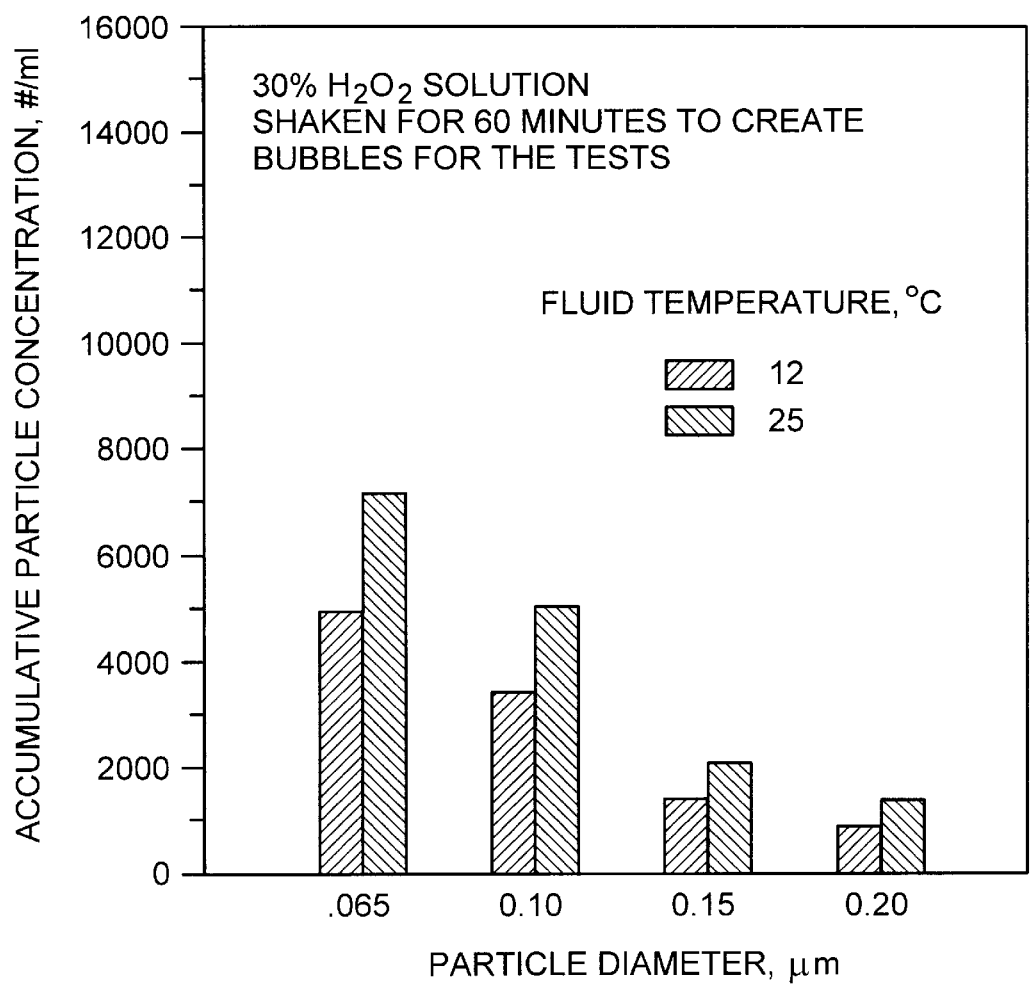
FIG. 3 is a histogram showing accumulative particle concentration in a hydrogen peroxide solution versus particle diameter.

Temperature and pressure of the samples were monitored with temperature and pressure sensors in the sampling line immediately downstream from the heat exchanger. The measurement results are shown in FIG. 3, which is a histogram of accumulative particle concentration versus particle diameter for the shaken samples. The measured particle concentrations in the sample at 12° C. were significantly lower than those in the sample at 25° C. The measured particle concentrations from the unshaken control sample (not shown) were substantially the same as those resulting from the shaken 12° C. sample. The lower particle counts for the 12° C. sample are indicative of micro-bubble suppression or elimination with decreasing sample temperature.

EXAMPLE 2

Figure 4:
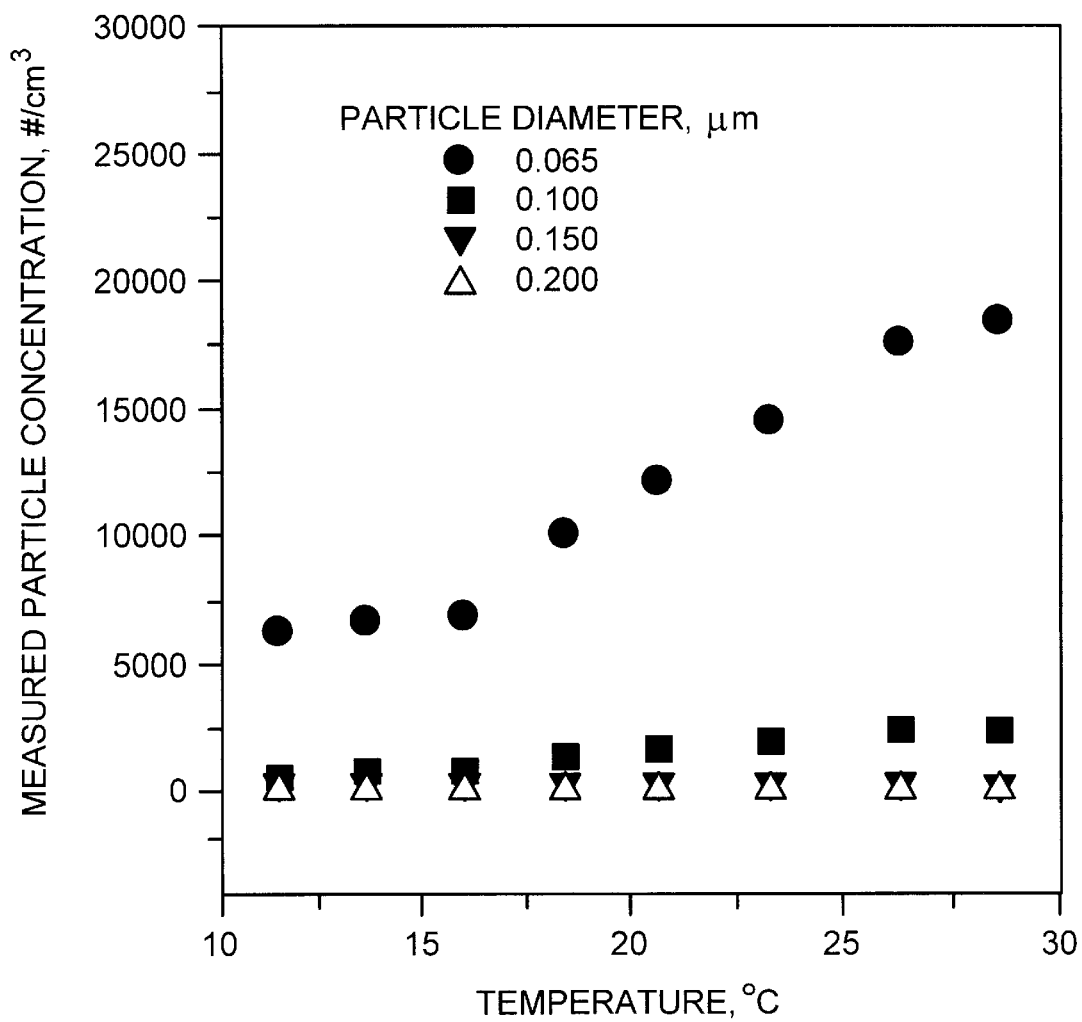
FIG. 4 is a graph of measured particle concentration in a hydrogen peroxide solution versus solution temperature.

Particle concentration in a 30% hydrogen peroxide solution for a number of different temperatures was investigated in this example. In particular, particle data for samples at eight temperatures between about 10° C. and 30° C. was obtained. The results of this example are illustrated in FIG. 4, which is a graph of measured particle concentration versus temperature.

It was found that the same trend of decreasing particle concentrations with lower temperature occurred by increasing the sample temperature from about 10° C. to 30° C. as well as by decreasing the temperature from about 30° C. to 10° C. For the hydrogen peroxide solution measured, the particle concentrations remained substantially the same after the temperature was decreased below about 18° C. Thus, micro-bubbles were effectively eliminated when the sample temperature was lower than about 18° C.

EXAMPLE 3

Figure 5:
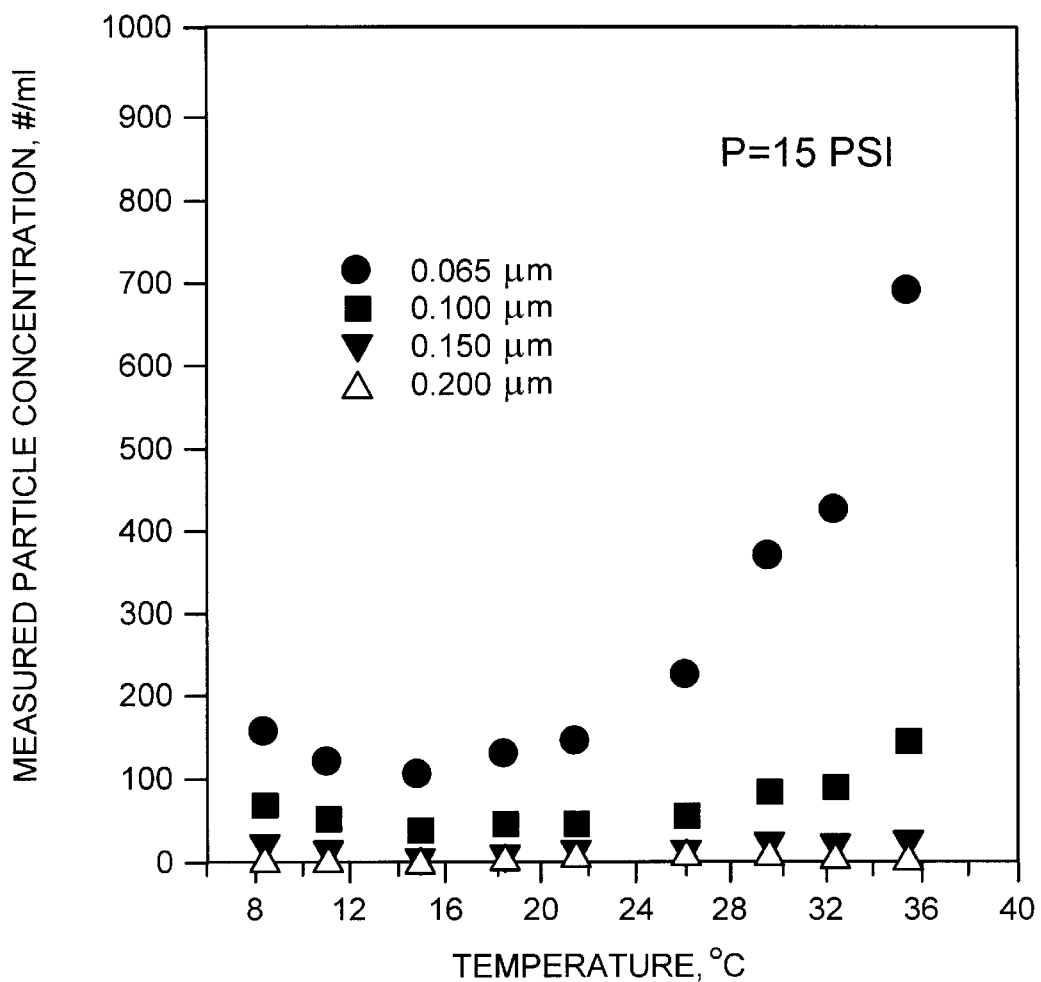
FIG. 5 is a graph of measured particle concentration in an ammonium hydroxide solution versus solution temperature.

Particle measurement data was also obtained for a 29% ammonium hydroxide ($NH_4OH$) solution at various temperatures between about 8° C. and 36° C. The procedure for this example was the same as that described above with reference to the hydrogen peroxide solution in Example 2, except for the specific temperatures investigated. The results from this example are illustrated in FIG. 5, which is a graph of measured particle concentration versus temperature.

A similar trend to that described above with reference to Example 2 was observed for this chemical. In particular, when the temperature was decreased below 18° C., to about 15° C., the measured particle concentrations were at their lowest point. At this point, the micro-bubbles were most completely suppressed.

It is noted that the elimination of micro-bubbles by reducing the sample temperature, in addition to being observed by the particle data output by the particle monitor, can also be monitored by observing the electric signals produced by the particles and micro-bubbles with an oscilloscope.

While the invention has been described in detail with reference to specific embodiments thereof, it will be apparent to those skilled in the art that various changes and modifications can be made, and equivalents employed, without departing from the scope of the appended claims.

What is claimed is:

1. A method of measuring particles in a liquid sample, comprising introducing a liquid sample into a heat exchanger, a step for controlling the temperature of the liquid sample exiting the heat exchanger to a predetermined temperature which is less than the temperature of the liquid sample entering the heat exchanger, and performing a particle measurement on said cooled sample by introducing said cooled sample into a particle detector.

2. The method according to claim 1, wherein the liquid sample is de-ionized water, ammonium hydroxide, hydrogen peroxide, sodium hydroxide, hydrofluoric acid, nitric acid, sulfuric acid, phosphoric acid, acetic acid, isopropyl alcohol, tetramethylammonium hydroxide, or a combination thereof.

3. The method according to claim 2, wherein the liquid sample is de-ionized water, ammonium hydroxide, hydrogen peroxide, or a combination thereof.

4. The method according to claim 1, wherein the heat exchanger comprises a container which holds a coolant fluid, and a hollow coil immersed in the fluid, wherein the liquid sample passes through the coil.

5. The method according to claim 4, wherein the liquid sample temperature is controlled by measuring the temperature of the liquid sample downstream from the heat exchanger and controlling, based on the measured temperature, the flow rate of coolant introduced into the heat exchanger.

6. The method according to claim 1, wherein the heat exchanger comprises a thermoelectric cooler in contact with a container holding the liquid sample.

7. The method according to claim 6, wherein the liquid sample is introduced into the heat exchanger through one side of the container and is removed therefrom through a second side of the container opposite the first side.

8. The method according to claim 7, wherein the container is rectangular in shape.

9. The method according to claim 6, wherein the liquid sample temperature is controlled by measuring the temperature of the liquid sample downstream from the heat exchanger and controlling, based on the measured temperature, the output of the thermoelectric cooler.

10. The method according to claim 1, wherein the predetermined temperature is below 18° C. and above the freezing point of the liquid sample.

11. The method according to claim 10, wherein the predetermined temperature is from 10 to 15° C.

12. The method according to claim 1, wherein the step for controlling the temperature of the liquid sample comprises measuring the temperature of the liquid sample downstream from the heat exchanger and controlling, based on the measured temperature, the flow rate of coolant introduced into the heat exchanger.

13. A system for measuring particles in a liquid sample, comprising:

a heat exchanger connected to receive a liquid sample from a liquid source;

an inlet conduit through which the liquid sample is introduced to the heat exchanger and an outlet conduit through which the liquid sample exits the heat exchanger;

means for controlling the temperature of the liquid sample exiting the heat exchanger to a predetermined temperature which is less than the temperature of the liquid sample entering the heat exchanger; and a particle detector connected to receive the cooled liquid sample from the heat exchanger.

14. The system according to claim 13, wherein the heat exchanger comprises a container which holds a coolant fluid and a hollow coil immersed in the fluid, wherein the liquid sample passes through the coil.

15. The system according to claim 13, wherein the heat exchanger comprises a thermoelectric cooler in contact with a container holding the liquid sample.

16. The system according to claim 15, wherein the temperature control means comprises a sensor for measuring the temperature of the sample exiting the heat exchanger, and one or more controller for controlling the output of the thermoelectric cooler based on the measured temperature.

17. The system according to claim 15, wherein the inlet conduit is connected to one side of the container and the outlet container is connected to the container through a second side of the container opposite the first side.

18. The system according to claim 17, wherein the container is rectangular in shape.

19. The system according to claim 13, wherein the temperature control means comprises a sensor for measuring the temperature of the sample exiting the heat exchanger, and one or more controller for controlling the flow rate of coolant introduced into the heat exchanger based on the measured temperature.

20. A system for measuring particles in a liquid sample, comprising:

a heat exchanger connected to receive a liquid sample from a liquid source, wherein the heat exchanger comprises a container which holds a coolant fluid and a hollow coil immersed in the fluid, wherein the liquid sample passes through the coil;

an inlet conduit through which the liquid sample is introduced to the heat exchanger and an outlet conduit through which the liquid sample exits the heat exchanger;

means for controlling the temperature of the liquid sample exiting the heat exchanger to a predetermined temperature which is less than the temperature of the liquid sample entering the heat exchanger; and a particle detector connected to receive the cooled liquid sample from the heat exchanger, wherein the temperature control means comprises a sensor for measuring the temperature of the sample exiting the heat exchanger, and one or more controller for controlling the flow rate of coolant introduced into the heat exchanger based on the measured temperature.

* * * * *